United States Patent
Nakano

(10) Patent No.: US 9,667,520 B2
(45) Date of Patent: May 30, 2017

(54) INTER-APPARATUS CONNECTION VERIFICATION SUPPORT SYSTEM, WEB SERVER APPARATUS AND INTER-APPARATUS CONNECTION VERIFICATION METHOD

(71) Applicant: Toshiba Medical Systems Corporation, Otawara-shi (JP)

(72) Inventor: Kenshi Nakano, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 449 days.

(21) Appl. No.: 14/521,938

(22) Filed: Oct. 23, 2014

(65) Prior Publication Data
US 2015/0046585 A1 Feb. 12, 2015

Related U.S. Application Data

(63) Continuation of application No. PCT/JP2013/073919, filed on Sep. 5, 2013.

(30) Foreign Application Priority Data

Sep. 6, 2012 (JP) .................................. 2012-196234
Sep. 5, 2013 (JP) .................................. 2013-183647

(51) Int. Cl.
*G06F 15/173* (2006.01)
*H04L 12/26* (2006.01)
(Continued)

(52) U.S. Cl.
CPC ............ *H04L 43/10* (2013.01); *A61B 5/0013* (2013.01); *A61B 5/7475* (2013.01); *A61B 6/563* (2013.01);
(Continued)

(58) Field of Classification Search
USPC ....... 709/203, 206, 217, 219, 223, 224, 226, 709/228, 231, 232, 238; 714/47.3;
(Continued)

(56) References Cited

U.S. PATENT DOCUMENTS 7,676,381 B2 * 3/2010 Kawakami ............. G06Q 10/10
705/2
7,822,499 B2 * 10/2010 Nakamura ....... G05B 19/41805
434/79
(Continued)

FOREIGN PATENT DOCUMENTS

JP 2003-116154 A 4/2003
JP 2006-285376 A 10/2006

OTHER PUBLICATIONS

International Search Report issued Oct. 8, 2013 in PCT/JP2013/073919 (with English language translation).

*Primary Examiner* — Quang N Nguyen
(74) *Attorney, Agent, or Firm* — Oblon, McClelland, Maier & Neustadt, L.L.P.

(57) ABSTRACT

A system includes a medical diagnostic imaging apparatus configured to generate medical images of subjects and to generate connection verification support information to be used by a connection-target apparatus to verify connection with medical diagnostic imaging apparatus; a peripheral apparatus expected to be connected with the medical diagnostic imaging apparatus via a communication network and configured to operate the medical images generated by the medical diagnostic imaging apparatus; and a web server apparatus configured to record the connection verification support information generated by the medical diagnostic imaging apparatus. The peripheral apparatus verifies connection with the medical diagnostic imaging apparatus by
(Continued)

using the connection verification support information acquired from the web server apparatus.

6 Claims, 5 Drawing Sheets

(51) Int. Cl.
| | | |
|---|---|---|
| G06Q 50/24 | (2012.01) | |
| G06Q 10/10 | (2012.01) | |
| A61B 5/00 | (2006.01) | |
| G06F 13/10 | (2006.01) | |
| A61B 6/00 | (2006.01) | |
| A61B 8/00 | (2006.01) | |
| G06F 19/00 | (2011.01) | |
| H04L 29/08 | (2006.01) | |
| A61B 5/055 | (2006.01) | |

(52) U.S. Cl.
CPC .............. *A61B 8/565* (2013.01); *G06F 13/10* (2013.01); *G06F 19/321* (2013.01); *G06F 19/3406* (2013.01); *G06Q 10/10* (2013.01); *G06Q 50/24* (2013.01); *H04L 67/02* (2013.01); *H04L 67/12* (2013.01); *A61B 5/0022* (2013.01); *A61B 5/0555* (2013.01)

(58) Field of Classification Search
USPC ..................... 705/2, 3; 704/235; 434/79; 1/1
See application file for complete search history.

(56) References Cited

U.S. PATENT DOCUMENTS

| | | | | |
|---|---|---|---|---|
| 9,235,973 | B2* | 1/2016 | Popescu | G08B 21/02 |
| 2010/0042434 | A1* | 2/2010 | Luo | G06F 19/321 |
| | | | | 705/3 |
| 2010/0256991 | A1* | 10/2010 | Ishikawa | G06F 19/321 |
| | | | | 705/3 |
| 2012/0316874 | A1* | 12/2012 | Lipman | G06Q 50/24 |
| | | | | 704/235 |
| 2013/0159788 | A1* | 6/2013 | Ashino | G06F 11/004 |
| | | | | 714/47.3 |
| 2017/0065361 | A1* | 3/2017 | Kurita | A61B 90/37 |

* cited by examiner

INTER-APPARATUS CONNECTION VERIFICATION SUPPORT SYSTEM, WEB SERVER APPARATUS AND INTER-APPARATUS CONNECTION VERIFICATION METHOD

CROSS-REFERENCE TO THE RELATED APPLICATION

This application is based on and claims the benefit of priority from International Application No. PCT/JP2013/073919, filed on Sep. 5, 2013, Japanese Patent Application No. 2012-196234, filed on Sep. 6, 2012 and Japanese Patent Application No. 2013-183647, filed on Sep. 5, 2013; the entire contents of which are incorporated herein by reference.

FIELD

Embodiments described herein relate generally to an inter-apparatus connection verification support system, a web server apparatus and an inter-apparatus connection verification method.

BACKGROUND

In recent years, medical diagnostic imaging apparatuses such as ultrasonic diagnosis apparatuses, for example, have been connected to various intra-hospital systems built in hospitals. Such connection enables medical images to be efficiently operated, for example, transferred, checked in a medical image storage and outputted to imagers, and thereby enables the medical images to be utilized for medical activities.

In communications of a medical diagnostic imaging apparatus with any of apparatuses constituting the intra-hospital system, the two apparatuses firstly establish connection therebetween through TCP/IP (Transmission Control Protocol/Internet Protocol), and then perform communications in accordance with DICOM (Digital Imaging and Communication in Medicine) communication protocol.

In this case, it is necessary to set various kinds of parameters required for the two apparatuses to perform DICOM communications therebetween, and most of the setting work is done through manual operations by an operator of the medical diagnostic imaging apparatus. For this reason, the setting requires a lot of time and effort, which is a situation where an error is likely to occur in the setting. In order to solve such problems, there has been proposed a method in which various parameters are preset in a medical diagnostic imaging apparatus and the set parameters are used as needed (see Japanese Patent Application Publication No. 2006-285376).

The above method, however, requires various parameters to be preset, and accordingly such setting still requires the effort and the like. Particularly recently, for ultrasonic diagnosis apparatuses, for example, a connection verification method in conformity with a measurement result SR (Structured Reporting) format has been employed. However, a general ultrasonic diagnosis apparatus supports a huge number of measurement and calculation items, specifically, about 4000 items, including combinations with the preset items of the apparatus.

Meanwhile, following recommendations of the DICOM standard, many vendors open the communication specifications of apparatuses to the public by presenting them in the document format called CS (Conformance Statement) on home pages of their companies.

In addition, a medical diagnostic imaging apparatus used in a hospital and, for example, a viewer apparatus configured to display the medical image acquired by the medical diagnostic imaging apparatus are manufactured by different companies in many cases. For this reason, under time and geographical constraints or security constraints, connection between a medical diagnostic imaging apparatus and a viewer apparatus needs to be verified before actual installation, and therefore it is often difficult to verify the connection by directly connecting the two apparatuses with each other.

DETAILED DESCRIPTION

Figure 1:
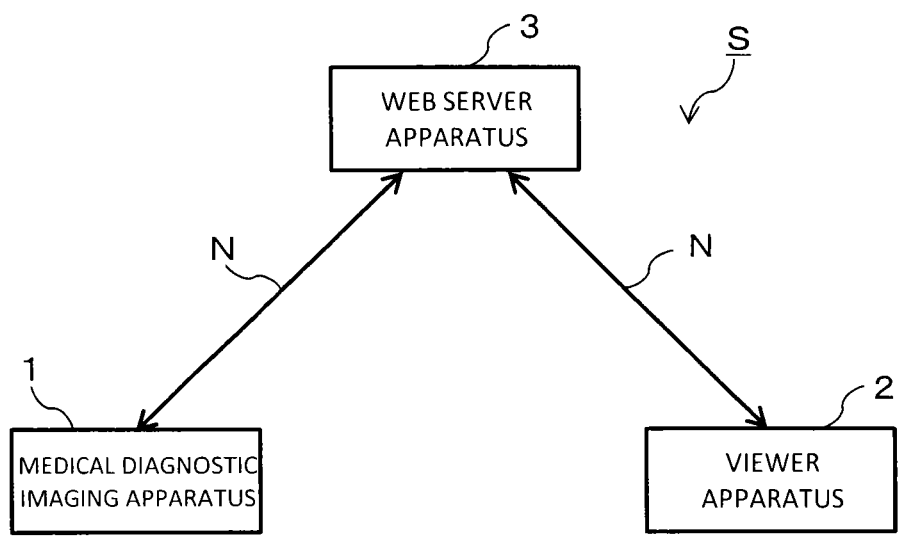
FIG. 1 is a block diagram showing an overall configuration of an inter-apparatus connection verification support system according to an embodiment.

According to an embodiment, an inter-apparatus connection verification support system includes a medical diagnostic imaging apparatus configured to generate a medical image of a subject and to generate connection verification support information to be used by a connection target apparatus to verify connection with the medical diagnostic imaging apparatus; a peripheral apparatus expected to be connected with the medical diagnostic imaging apparatus via a communication network and configured to operate the medical image generated by the medical diagnostic imaging apparatus; and a web server apparatus configured to record the connection verification support information generated by the medical diagnostic imaging apparatus. The peripheral apparatus verifies connection with the medical diagnostic imaging apparatus by using the connection verification support information acquired from the web server apparatus.

According to another embodiment, a web server apparatus configured to post connection verification support information to be used by a peripheral apparatus, which is configured to display a medical image generated by a medical diagnostic imaging apparatus, to verify connection with the medical diagnostic imaging apparatus includes: an information reception unit configured to receive request items, and information on specifications of the medical diagnostic imaging apparatus; and a support information generator unit configured to generate the connection verification support information to be used by the peripheral apparatus to verify the connection, on the basis of the specification information outputted from the medical diagnostic imaging apparatus and the request items outputted from the peripheral apparatus.

According to still another embodiment, an inter-apparatus connection verification method includes the steps of: identifying a request item in a peripheral apparatus, which is configured to display a medical image generated by a medical diagnostic imaging apparatus, in verifying connection between the peripheral apparatus and the medical diagnostic imaging apparatus; identifying, as request item information, a specification item matched with the request item from specification information of the medical diagnostic imaging apparatus, and posting the request item information as connection verification support information on a web server apparatus; causing the peripheral apparatus to acquire the connection verification support information posted on the web server apparatus and to perform matching of the connection verification support information with the request item; and completing the verifying of the connection between the peripheral apparatus and the medical diagnostic imaging apparatus by completing the matching.

According to yet another embodiment, an inter-apparatus connection verification method includes the steps of: causing a peripheral apparatus, which is expected to be connected with a medical diagnostic imaging apparatus configured to generate a medical image, to identify a request item needed to verify connection with the medical diagnostic imaging apparatus, and send the request item to a web server apparatus; causing the medical diagnostic imaging apparatus to acquire the request item from the web server apparatus; identifying, as request item information, information matched with the request item from specification information of the medical diagnostic imaging apparatus, and posting the request item information as connection verification support information on the web server apparatus; and causing the peripheral apparatus to acquire the connection verification support information and perform matching of the connection verification support information with the request item; and completing the verifying of the connection between the peripheral apparatus and the medical diagnostic imaging apparatus by completing the matching.

Hereinafter, embodiments of the present invention will be described in details with reference to the drawings.

First Embodiment

FIG. 1 is a block diagram showing an overall configuration of an inter-apparatus connection verification support system S according to an embodiment. The inter-apparatus connection verification support system S includes a medical diagnostic imaging apparatus 1, a viewer apparatus 2 which is an example of a peripheral apparatus, and a web server apparatus 3.

The medical diagnostic imaging apparatus 1 is an apparatus to capture interior information of a subject and to generate a medical image. Apparatuses applicable as the medical diagnostic imaging apparatus 1 are, for example, an ultrasonic diagnosis apparatus, an x-ray computed tomography (CT) apparatus, a magnetic resonance imaging (MRI) apparatus and the like. Note that the following description is provided by taking an ultrasonic diagnosis apparatus as an example of the medical diagnostic imaging apparatus 1.

Figure 2:
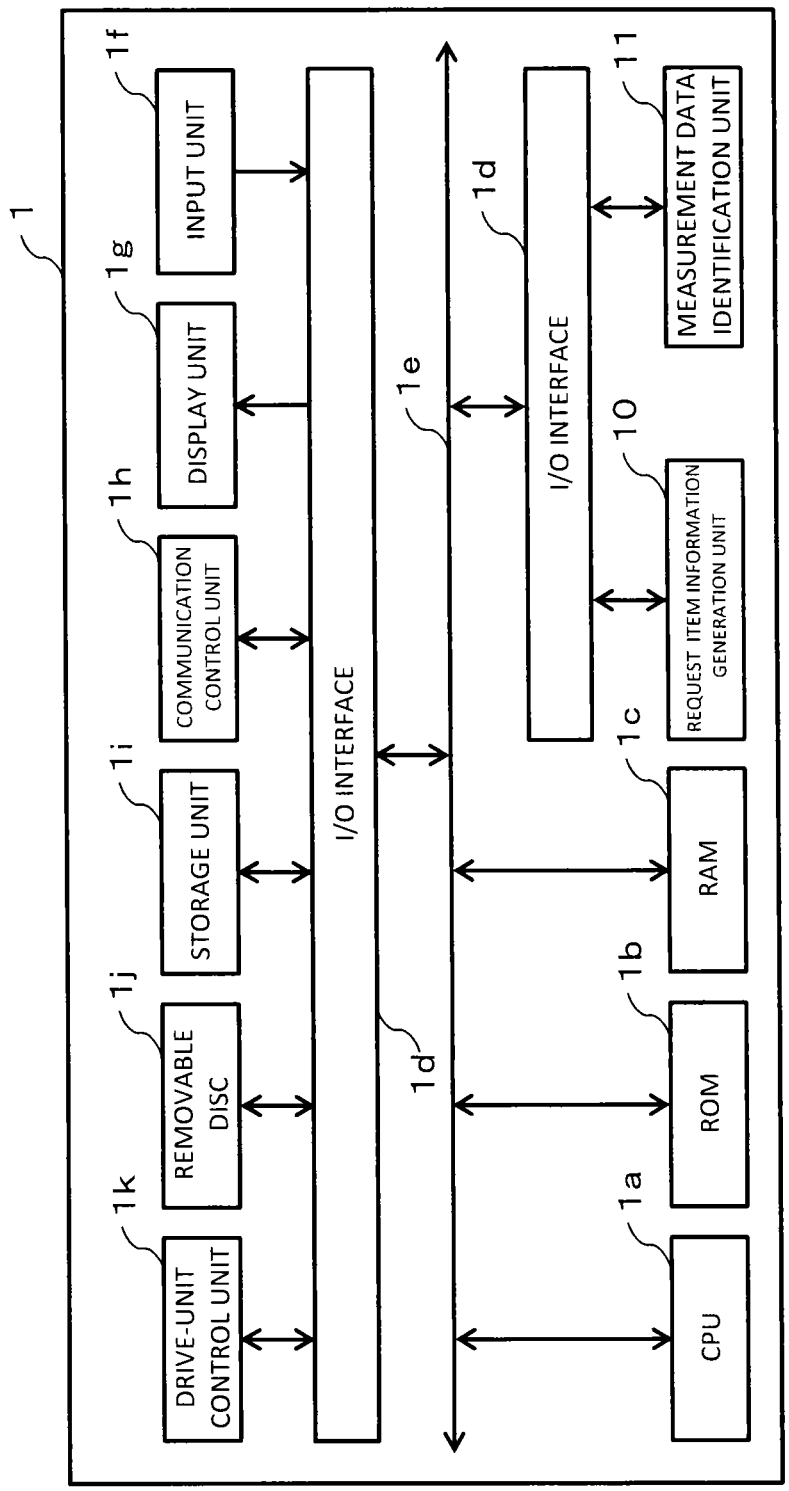
FIG. 2 is a block diagram showing the internal configuration of the medical diagnostic imaging apparatus 1 in the embodiment.

FIG. 2 is a block diagram showing the internal configuration of the medical diagnostic imaging apparatus 1 in the embodiment.

In the medical diagnostic imaging apparatus 1, a CPU (Central Processing Unit) 1a being a controller, a ROM (Read Only Memory) 1b, a RAM (Random Access Memory) 1c, and an I/O interface 1d are connected with one another via a bus 1e. The I/O interface 1d is connected with an input unit 1f, a display unit 1g, a communication control unit 1h, a storage unit 1i, a removable disc 1j, and a driving-unit control unit 1k.

The driving-unit control unit 1k controls a driving unit (not shown in FIG. 1) which drives each part of the medical diagnostic imaging apparatus 1.

Moreover, a request item information generation unit 10 and a measurement data identification unit 11 are connected to the I/O interface 1d in order that information, which is to be used to verify connection with the viewer apparatus 2 and is customized for the connection target viewer apparatus 2, can be generated from specifications of the medical diagnostic imaging apparatus 1.

The CPU 1a executes a boot program for starting the medical diagnostic imaging apparatus 1 by reading the program from the ROM 1b on the basis of an input signal from the input unit 1f, and reads various operating systems stored in the storage unit 1i. The CPU 1a also controls various devices on the basis of input signals from other external equipment which are not shown in FIG. 1.

Further, the CPU 1a reads programs and data stored in the RAM 1c, the storage unit 1i, and the like and loads them onto the RAM 1c. Moreover, the CPU 1a is a processor that implements series of processing, such as generation of the specifications to be used to verify the connection with the viewer apparatus 2 and generation of a medical image, on the basis of commands of the programs read from the RAM 1c.

The input unit 1f is configured with an input device, such as a keyboard or a dial, with which the user (e.g., a doctor or a technologist) of the medical diagnostic imaging apparatus 1 inputs various operations. The input unit 1f generates an input signal based on the operation made by the user, and sends the input signal to the CPU 1a via the bus 1e.

In some cases, the medical diagnostic imaging apparatus 1 is provided with a dedicated operation penal in addition to the keyboard or the like. In this case, the user can perform operations on an operation screen (a display unit to be described later) via an input device on the operation panel.

The display unit 1g is, for example, a liquid crystal display. The display unit 1g receives an output signal from the CPU 1a via the bus 1e. The display unit 1g is means for displaying information to be used to perform connection verification, generated medical images, processing results of the CPU 1a, and the like.

The communication control unit 1h is means, such as a LAN card or a modem, capable of connecting the medical diagnostic imaging apparatus 1 to the communication network such as the Internet or a LAN which are not illustrated. Data exchanged through the communication network via the communication control unit 1h are sent to and received from the CPU 1a via the I/O interface 1d and the bus 1e, as an input signal or an output signal. For example, medical images, measurement and calculation results, and the like generated in the medical diagnostic imaging apparatus 1 are sent in the format defined by the DICOM standard.

The storage unit 1i is configured of a semiconductor or a magnetic disc. In the storage unit 1i, stored are a program to be executed by the CPU 1a to capture ultrasonic images (medical images) and specification information of the medical diagnostic imaging apparatus 1 itself.

The removable disc 1j is an optical disc or a flexible disc, and signals read or written by a disc drive are sent to and received from the CPU 1a via the I/O interface 1d and the bus 1e.

Having the foregoing configuration, the medical diagnostic imaging apparatus (ultrasonic diagnosis apparatus) 1 according to the embodiment of the present invention has a function to collect interior information on a subject by using ultrasonic waves, and additionally has a function to perform connection verification processing in collaboration with the viewer apparatus 2 on which medical images captured by the medical diagnostic imaging apparatus (ultrasonic diagnosis apparatus) 1 are to be displayed.

The request item information generation unit 10 selects appropriate specifications from all the specifications of the medical diagnostic imaging apparatus 1 according to specification items requested by the viewer apparatus 2 of a connection target with the medical diagnostic imaging apparatus 1, and thereby generates information on the appropriate specifications, namely, request item information.

The measurement data identification unit 11 identifies measurement data of a medical image in conformance with the request items on the basis of the request item information generated by the request item information generation unit 10.

The viewer apparatus 2 to be connected with the medical diagnostic imaging apparatus 1 performs connection verification processing on the basis of the request item information and the measurement data. For this reason, hereinafter, the request item information and the measurement data are collectively referred to as "connection verification support information" as needed.

The viewer apparatus 2 is one of peripheral apparatuses connected to the communication network N, and is an apparatus which displays medical images and measurement and calculation results collected and generated by the medical diagnostic imaging apparatus 1 in order for doctors or the like to check the medical images and others or do the like in bedside medical treatments, for example. Moreover, the viewer apparatus 2 may have a function to store these medical images and others.

It should be noted that the embodiment is based on the assumption that the viewer apparatus 2 is fabricated by a manufacturer different from that of the medical diagnostic imaging apparatus 1. On the other hand, the medical diagnostic imaging apparatus 1 and the web server apparatus 3 may be fabricated by the same manufacturer or different manufacturers.

The web server apparatus 3 is a server apparatus with which the medical diagnostic imaging apparatus 1 and the viewer apparatus 2 are connected via the communication network N with a web browser defined. The foregoing CS of the medical diagnostic imaging apparatus 1 is posted on the web server apparatus 3. Thus, the viewer apparatus 2, for example, performs connection verification processing by receiving items appropriate for the viewer apparatus 2 when necessary from the CS on the medical diagnostic imaging apparatus 1 to be connected with the viewer apparatus 2 and by checking the received items against its own specifications (items) and the like.

The communication network N connects the medical diagnostic imaging apparatus 1 and the viewer apparatus 2 with the web server apparatus 3. Thus, specification information (connection verification support information) of the medical diagnostic imaging apparatus 1 and the information on the request items of the viewer apparatus 2, for example, can be exchanged between the medical diagnostic imaging apparatus 1 and the web server apparatus 3 or between the viewer apparatus 2 and the web server apparatus 3. An example citable as the communication network N is a network such as a LAN (Local Area Network) or the Internet.

Here, the medical diagnostic imaging apparatus 1 and the web server apparatus 3 or the web server apparatus 3 and the viewer apparatus 2 perform communications therebetween by using communication protocol such as HTTP (Hyper Text Transfer Protocol), for example. In addition, the apparatuses communicate commands in a markup language such as HTML (Hyper Text Markup Language) or XML (Extensible Markup Language), and an application program for dynamic processing by using CGI (Common Gateway Interface) or the like is operated on the web server apparatus 3.

Note that, in the inter-apparatus connection verification support system S shown in FIG. 1, only one medical diagnostic imaging apparatus 1, one viewer apparatus 2 and one web server apparatus 3 are shown for convenience in the description. However, the numbers of these apparatuses connected to the communication network N may be one or be two or more.

Figure 3:
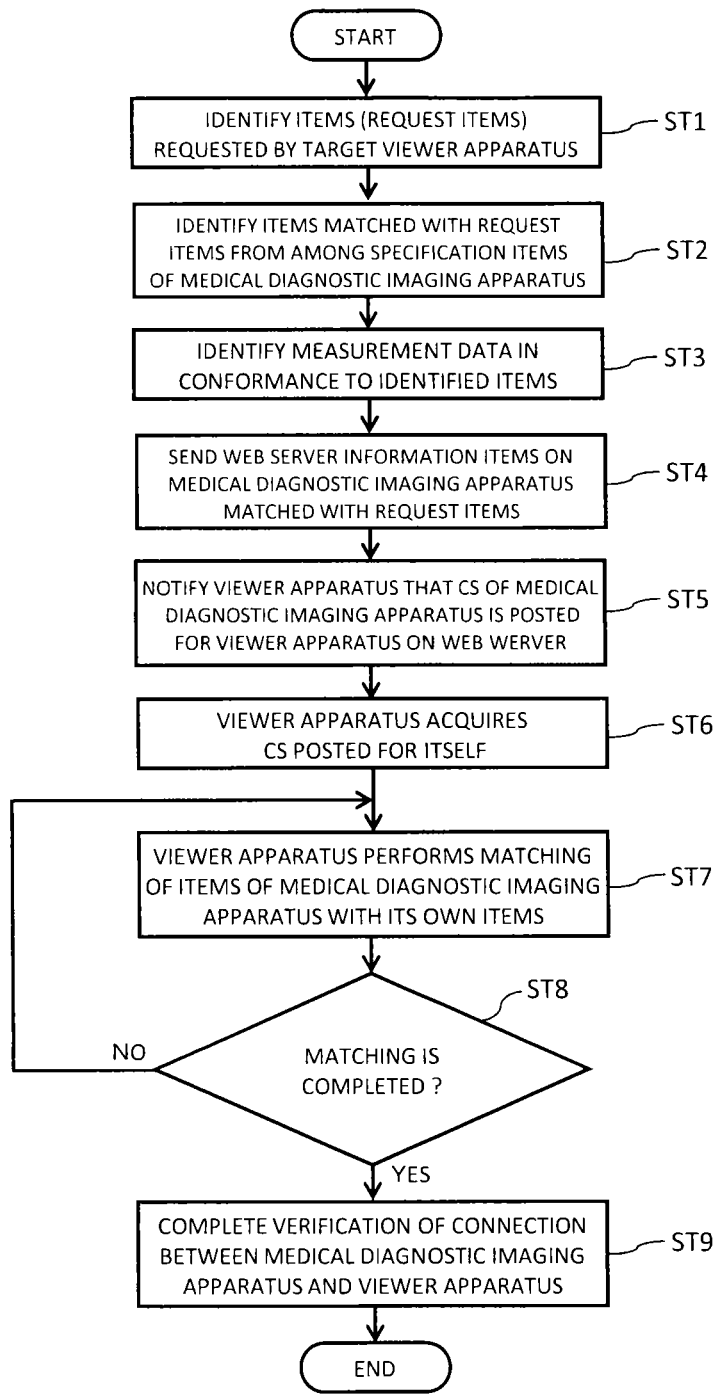
FIG. 3 is a flowchart showing a flow of an inter-apparatus connection verification method according to a first embodiment.

FIG. 3 is a flowchart showing a flow of an inter-apparatus connection verification method in the first embodiment. As a prerequisite for the viewer apparatus 2 to display the medical images and measurement and calculation results generated by the medical diagnostic imaging apparatus 1, it is necessary to check whether or not these kinds of information are information displayable on the viewer apparatus 2. This checking work is the connection verification. For example, if a viewer apparatus 2 is newly installed in a medical institution, a medical diagnostic imaging apparatus 1 and the viewer apparatus 2 may be directly connected with each other and then may be checked as to whether or not the apparatuses are appropriately connected with each other (connection verification).

However, the connection verification may be under the aforementioned time and geographical constraints in some possible cases such as one where the development departments of the vendors of the two apparatuses to be checked for the connection verification are located at different countries. In other some cases, a company or a medical institution at present often builds an internal network with the security of network communications enhanced by connecting the network to the outside via, for example, a firewall or the like, instead of connecting the network directly to the outside. For this reason, in many cases, a security constraint is imposed in which a new apparatus is not easily allowed to connect with the medical diagnostic imaging apparatus 1 already installed in the hospital.

Under these circumstances, the following inter-apparatus connection verification method is employed in order to enable the connection verification between the medical diagnostic imaging apparatus 1 and the viewer apparatus 2 despite the presence of these constraints. In this inter-apparatus connection verification method, the viewer apparatus 2 performs the connection verification by using the CS of the medical diagnostic imaging apparatus 1 posted on the web server apparatus 3, while the two apparatuses are not directly connected with each other.

Firstly, the method involves identifying items (request items) requested by the viewer apparatus 2 of a connection target with the medical diagnostic imaging apparatus 1 (ST1). Specifically, the medical diagnostic imaging apparatus 1 is configured to support a huge number of specifications such for example as measurement or calculation methods as described above. In order for the viewer apparatus 2 to display information generated by the medical diagnostic imaging apparatus 1, the specifications of the viewer apparatus 2 need to conform to the specifications of the information to be displayed from among such a huge number of specifications. The connection verification is to check whether the conformance of all the specifications is assured. To this end, firstly, it is necessary to identify which specifications are requested by the viewer apparatus 2.

In identification of the request items of the viewer apparatus 2, the items requested by the viewer apparatus 2 are identified, for example, based on a report sent from a medical institution where the viewer apparatus 2 is to be installed. The items requested by the viewer apparatus 2 are known best by the medical institution where the viewer apparatus 2 is to be introduced, but are difficult to know on the medical diagnostic imaging apparatus 1 side. In addition, it is often the case that the viewer apparatus 2 is a product fabricated by a manufacturer different from the manufacturer of the medical diagnostic imaging apparatus 1. In this case, in view of the time and geographical constraints, it is considered that the information on the viewer apparatus 2 can be acquired more easily from a person belonging to the medical institution where the medical diagnostic imaging apparatus 1 is already installed and the viewer apparatus 2 is to be newly introduced, than through direct communication of the vendor of the medical diagnostic imaging apparatus 1 with the vendor of the viewer apparatus 2.

The medical diagnostic imaging apparatus 1 specifies the request items notified by the viewer apparatus 2 and identifies which one of the items constituting its own specifications is matched with each of the request items (ST2). Then, the medical diagnostic imaging apparatus 1 extracts only the identified specifications. The extracted specifications of the medical diagnostic imaging apparatus 1 are matched with the request items of the viewer apparatus 2 of the connection target, and thus are referred to as "request item information" below.

This request item information is posted on the web server apparatus 3. Thus, from among a huge number of specifications of the medical diagnostic imaging apparatus 1, the specifications customized to the requests of the viewer apparatus 2 are posted for the viewer apparatus 2. Then, when accessing the web server apparatus 3, the viewer apparatus 2 can easily find and acquire the information necessary for the connection verification. This series of processing is performed by the request item information generation unit 10 of the medical diagnostic imaging apparatus 1.

Moreover, the measurement data identification unit 11 identifies the measurement data (measurement and calculation results) based on the request item information (ST3). The measurement data herein is what is termed "SR data" and is important information for an operator who actually operates the viewer apparatus 2. Even though the request item information is generated based on the request items notified of by the viewer apparatus 2, there is a possibility that two or more similar specifications may be contained in the request item information. Specifically, when measurements are performed even on the same area at the same intervals, for example, the obtained measurement data are different depending on the specification items.

The measurement data identification unit 11 identifies measurement data in conformance with each of the specifications. Then, the CPU 1a sends the measurement data and the request item information generated by the request item information generation unit 10 as the connection verification support information to the web server apparatus 3 via the communication control unit 1h (ST4). Here, the connection verification support information conforms to the DICOM standard.

The connection verification support information sent from the medical diagnostic imaging apparatus 1 via the communication network N is posted, for example, in the CS format on the web server apparatus 3. The sent connection verification support information includes an IP address of the viewer apparatus 2 to be connected with the medical diagnostic imaging apparatus 1, in addition to the foregoing request item information and measurement data.

When the connection verification support information is posted on the web server apparatus 3, the target viewer apparatus 2 is notified that the CS (connection verification support information) for the viewer apparatus 2 has been sent from the medical diagnostic imaging apparatus 1 and is now posted on the web server apparatus 3 (ST5). The viewer apparatus 2 basically cannot know whether or not the connection verification support information sent from the medical diagnostic imaging apparatus 1 is posted on the web server apparatus 3. Moreover, the viewer apparatus 2 is not yet connected with the medical diagnostic imaging apparatus 1. For these reasons, the web server apparatus 3 notifies the viewer apparatus 2 of that information.

In this regard, the web server apparatus 3 identifies for which viewer apparatus 2 the CS (connection verification support information) is posted on the web server apparatus 3, on the basis of the IP address of the connection-target viewer apparatus 2 contained in the above connection verification support information, for example, and notifies the identified viewer apparatus 2 of that information.

The viewer apparatus 2 thus notified acquires the connection verification support information posted for the viewer apparatus 2 itself on the web server apparatus 3 (ST6). Then, the viewer apparatus 2 performs matching of its own specification items on the basis of the connection verification support information (ST7). Since the connection verification support information is primarily formed by collecting the items according to the request items sent from the viewer apparatus 2, it seems to be natural that this matching processing is usually completed without any problem.

Then, whether all the matching processing is completed or not is judged (ST8). If the matching processing is judged as completed, the processing for verifying the connection between the medical diagnostic imaging apparatus 1 and the viewer apparatus 2 is completed (ST9). Under this condition, the medical diagnostic imaging apparatus 1 and the viewer apparatus 2 just have to be actually directly connected with each other, so that various kinds of information such as medical images sent from the medical diagnostic imaging apparatus 1 can be displayed on the viewer apparatus 2 according to needs.

As has been described above, connection between a medical diagnostic imaging apparatus and a peripheral apparatus (viewer apparatus) which are fabricated by different manufacturers can be verified by using the connection verification support information of the medical diagnostic imaging apparatus posted on a web server apparatus. Thus, it is possible to provide an inter-apparatus connection verification support system, a web server apparatus and an inter-apparatus connection verification method which, even under various constraints, are capable of verifying connection between a peripheral apparatus (viewer apparatus) and a medical diagnostic imaging apparatus not by directly connecting the two apparatus with each other but by selecting only information items appropriate for the peripheral apparatus from a huge number of information items of the medical diagnostic imaging apparatus.

In particular, the connection verification support information posted on the web server apparatus is generated in advance according to the specifications of the viewer apparatus to be connected with the medical diagnostic imaging apparatus. Thus, the information necessary and sufficient for the view apparatus can be automatically acquired without omission from a huge number of items of specification information of the medical diagnostic imaging apparatus. This processing is easier and more reliable than the work in which an operator manually extracts the information necessary for the viewer apparatus from the specifications of the medical diagnostic imaging apparatus.

In addition, in the foregoing inter-apparatus connection verification support system, the medical diagnostic imaging apparatus and the viewer apparatus are not connected with each other. However, the medical diagnostic imaging apparatus and the web server apparatus are connected with each other and the web server apparatus and the viewer apparatus are connected with each other. Thus, the medical diagnostic imaging apparatus and the viewer apparatus can exchange information therebetween by way of the web server apparatus. Hence, the viewer apparatus can acquire the connection verification support information generated by the medical diagnostic imaging apparatus and sent to the web server apparatus. By employing such an inter-apparatus connection verification support system, connection between a medical diagnostic imaging apparatus and a viewer apparatus can be verified without consideration of various constraints such as time and geographical constraints or security constraints.

Second Embodiment

Next, a second embodiment of the present invention will be described. In the second embodiment, the same constituents as the constituents described above in the first embodiment will be designated by the same reference numerals and duplicate explanation of the same constituents will be omitted herein.

Figure 4:
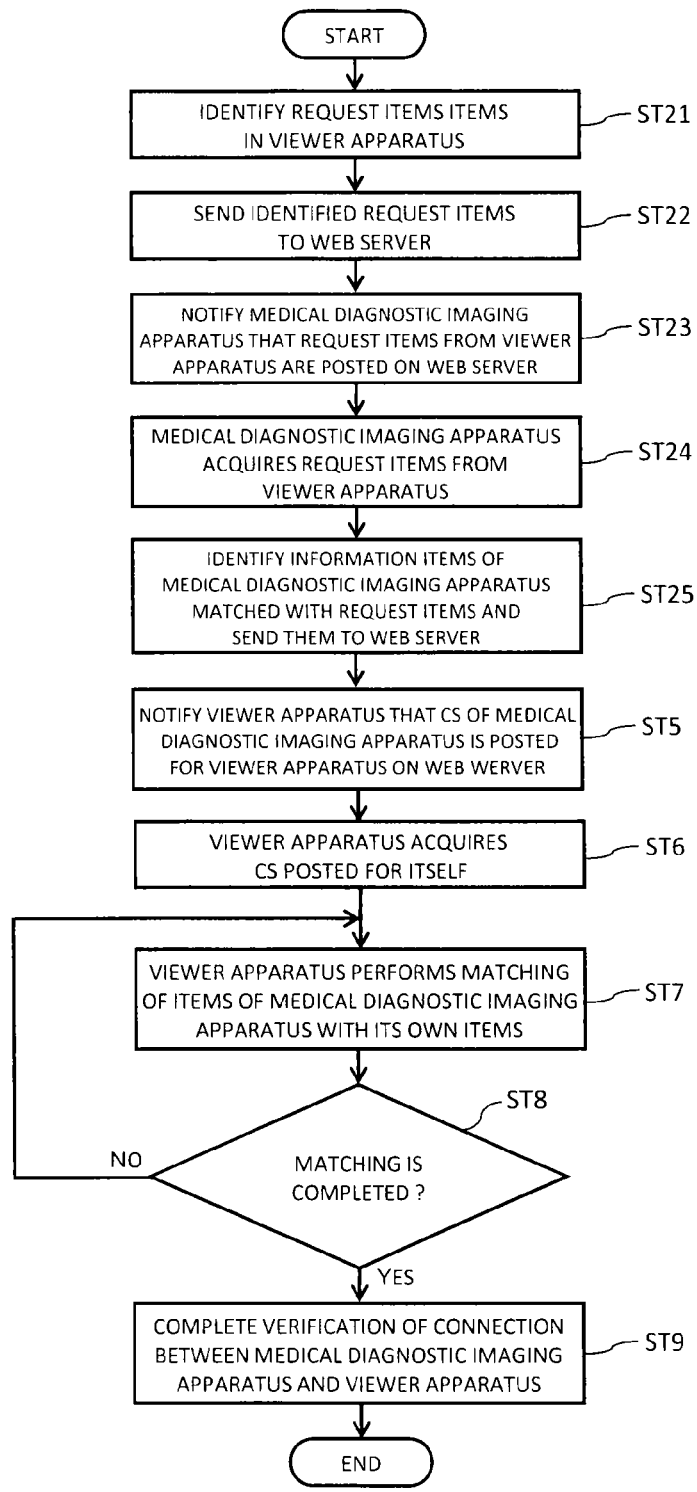
FIG. 4 is a flowchart showing a flow of an inter-apparatus connection verification method according to a second embodiment.

The second embodiment employs a different method of verifying connection between a medical diagnostic imaging apparatus and a viewer apparatus. FIG. 4 is a flowchart showing a flow of the inter-apparatus connection verification method in the second embodiment.

The first embodiment takes the procedure in which a medical institution where the viewer apparatus 2 is to be installed identifies in advance the request items which the viewer apparatus 2 requests from the medical diagnostic imaging apparatus 1, and the medical diagnostic imaging apparatus 1 generates the connection verification support information on the basis of the identified request items. The inter-apparatus connection verification method in the second embodiment is different in that the viewer apparatus 2 to be installed notifies the medical diagnostic imaging apparatus 1 of the request items via the web server apparatus 3.

In the second embodiment, the viewer apparatus 2 to be connected with the medical diagnostic imaging apparatus 1 firstly identifies its own request items (ST21). This means to identify the specifications supported by the viewer apparatus 2 from among the specifications of the medical diagnostic imaging apparatus 1.

After that, the viewer apparatus 2 sends the request items to the web server apparatus 3 (ST22). The request items sent to the web server apparatus 3 from the viewer apparatus 2 include information on the IP address of the medical diagnostic imaging apparatus 1 to be connected with the viewer apparatus 2.

The web server apparatus 3 having received the request items from the viewer apparatus 2 notifies the connection-target medical diagnostic imaging apparatus 1 that the request items are posted on the web server apparatus 3 (ST23).

On the basis of the notification from the web server apparatus 3, the medical diagnostic imaging apparatus 1 acquires the request items of the viewer apparatus 2 from the web server apparatus 3 (ST24). In the medical diagnostic imaging apparatus 1, the request item information generation unit 10 extracts specifications matched with the acquired request items from its own specifications, and the measurement data identification unit 11 identifies the measurement data in conformance with the extracted specifications. The connection verification support information appropriate for the request items is generated through these processing steps.

The connection verification support information thus generated is sent from the medical diagnostic imaging apparatus 1 to the web server apparatus 3, and is posted on the web server apparatus 3 (ST25).

The following steps in the flow are the same as those in the first embodiment. Specifically, the web server apparatus 3 notifies the viewer apparatus 2 to be connected with the medical diagnostic imaging apparatus 1 that the connection verification support information generated for the target viewer apparatus 2 is posted on the web server apparatus 3 (ST5). The viewer apparatus 2 thus notified receives the connection verification support information from the web server apparatus 3, and performs the matching processing of the connection verification support information with its own specifications (ST6 and ST7). When the matching is completed, the processing of verifying the connection between the medical diagnostic imaging apparatus 1 and the viewer apparatus 2 can be regarded as completed (ST9). Thereafter, the two apparatuses are actually connected with each other.

As has been described above, connection between a medical diagnostic imaging apparatus and a peripheral apparatus (viewer apparatus) which are fabricated by different manufacturers can be verified by using the connection verification support information of the medical diagnostic imaging apparatus posted on a web server apparatus. Thus, it is possible to provide an inter-apparatus connection verification support system, a web server apparatus and an inter-apparatus connection verification method which, even under various constraints, are capable of verifying connection between a peripheral apparatus (viewer apparatus) and a medical diagnostic imaging apparatus not by directly connecting the two apparatus with each other but by selecting only information items appropriate for the peripheral apparatus from a huge number of information items of the medical diagnostic imaging apparatus.

Moreover, even under various constraints, the second embodiment also enables easy and reliable extraction and matching of the specifications and the like appropriate for the viewer apparatus from among a huge number of specifications of the medical diagnostic imaging apparatus, as described in the first embodiment. Since the request items are directly sent from the viewer apparatus to the web server apparatus, in particular, the vendors of the medical diagnostic imaging apparatus and the viewer apparatus for which the connection verification needs to be performed are both allowed to attend the connection verification processing at more flexible timing. Thus, the time and geographical constraints are more relaxed.

Third Embodiment

Next, a third embodiment of the present invention will be described. In the third embodiment, the same constituents as the constituents described above in the first embodiment or the second embodiment will be designated by the same reference numerals and duplicate explanation of the same constituents will be omitted herein.

A web server apparatus 3A in the third embodiment is different from the web server apparatus 3 in the first or second embodiment in that the web server apparatus 3A, in place of a medical diagnostic imaging apparatus 1, generates connection verification support information for a viewer apparatus 2.

Figure 5:
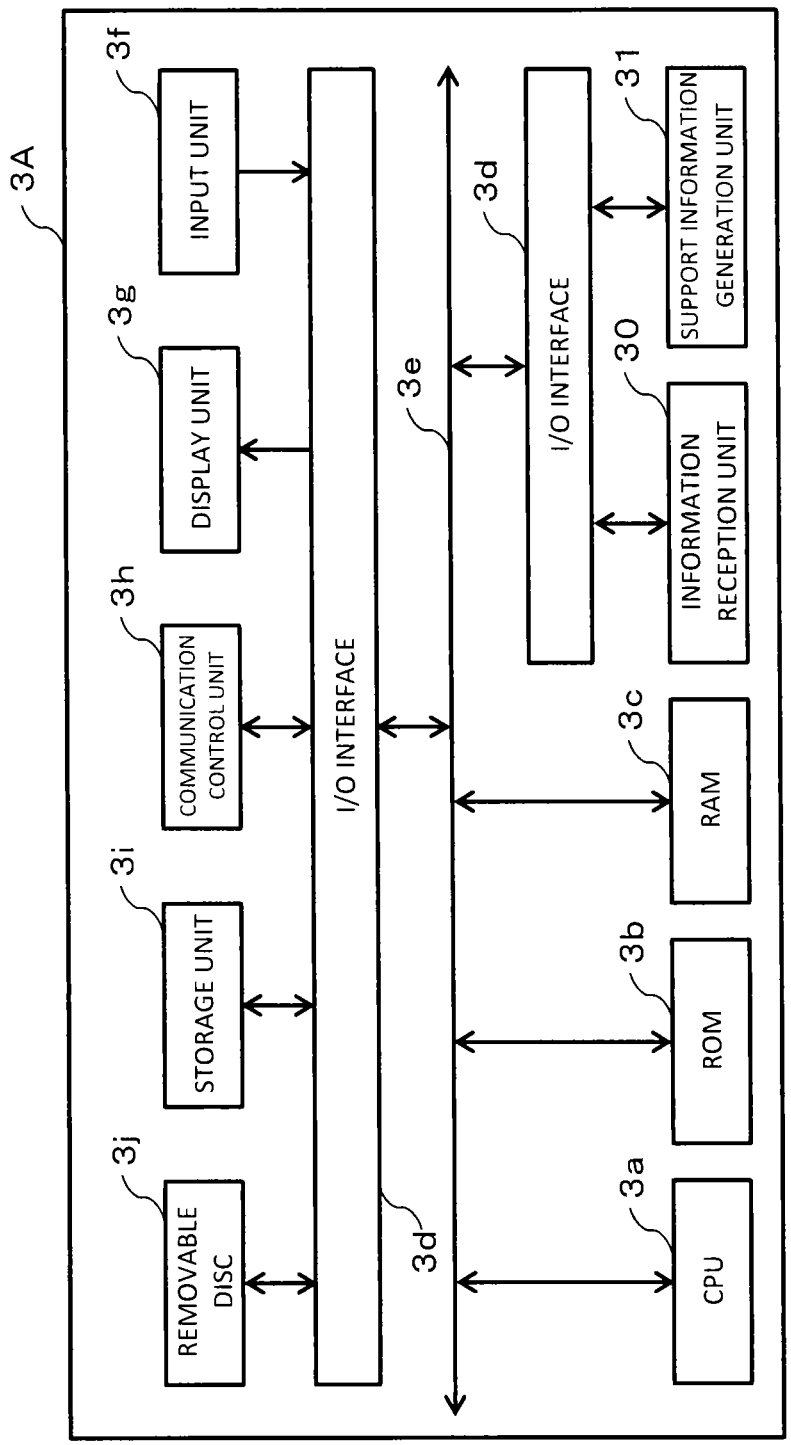
FIG. 5 is a block diagram showing an internal configuration of a web server apparatus in a third embodiment.

FIG. 5 is a block diagram showing an internal configuration of the web server apparatus 3A in the third embodiment. In the web server apparatus 3A, a CPU (Central Processing Unit) 3a, a ROM (Read Only Memory) 3b, a RAM (Random Access Memory) 3c and an I/O interface 3d are connected with each other via a bus 3e. An input unit 3f, a display unit 3g, a communication control unit 3h, a storage unit 3i and a removable disk 3j are connected to the I/O interface 3d. In addition, an information reception unit 30 and a support information generation unit 31 are also connected to the I/O interface 3d. The information reception unit 30 receives information sent from the medical diagnostic imaging apparatus 1 and the viewer apparatus 2.

The information reception unit 30 receives specification information of the medical diagnostic imaging apparatus 1 from the medical diagnostic imaging apparatus 1. The specification information mentioned herein is information purely containing all the specifications of the medical diagnostic imaging apparatus 1 and including measurement data, because the medical diagnostic imaging apparatus 1 does not receive request items of the viewer apparatus 2. Meanwhile, the information reception unit 30 receives request items from the viewer apparatus 2.

The support information generation unit 31 generates connection verification support information necessary for verifying connection between the viewer apparatus 2 and the medical diagnostic imaging apparatus 1 on the basis of the specification information of the medical diagnostic imaging apparatus 1 and the request items of the viewer apparatus 2 which have been sent to the information reception unit 30.

In summary, the third embodiment is characterized in that the web server apparatus 3A collects necessary information from both of the medical diagnostic imaging apparatus 1 and the viewer apparatus 2 which are connection targets, and generates the connection verification support information necessary for the viewer apparatus 2 to perform connection verification.

In the third embodiment, the web server apparatus 3A firstly receives the foregoing information at the information reception unit 30 from both the medical diagnostic imaging apparatus 1 and the viewer apparatus 2. Specifically, the vendor of the medical diagnostic imaging apparatus 1 and the vendor of the viewer apparatus 2 each identify its own connection target apparatus when necessary. Then, the medical diagnostic imaging apparatus 1 sends its own specifications to the web server apparatus 3A, while the viewer apparatus 2 sends the request items to the web server apparatus 3A. Thereafter, the web server apparatus 3A generates the connection verification support information at the support information generation unit 31 on the basis of the received information, and notifies the connection-target viewer apparatus 2 that the connection verification support information is generated.

The viewer apparatus 2 thus notified receives the connection verification support information from the web server apparatus 3A, and verifies connection with the medical diagnostic imaging apparatus 1 on the basis of the connection verification support information.

As has been described above, connection between a medical diagnostic imaging apparatus and a peripheral apparatus (viewer apparatus) which are fabricated by different manufacturers can be verified by using the connection verification support information generated by a web server apparatus. Thus, it is possible to provide an inter-apparatus connection verification support system, a web server apparatus and an inter-apparatus connection verification method which, even under various constraints, are capable of verifying connection between a peripheral apparatus (viewer apparatus) and a medical diagnostic imaging apparatus not by directly connecting the two apparatus with each other but by selecting only information items appropriate for the peripheral apparatus from a huge number of information items of the medical diagnostic imaging apparatus.

In particular, if the web server apparatus is provided with the foregoing function, the medical diagnostic imaging apparatus having more specific functions can be provided, because the medical diagnostic imaging apparatus does not need to have the function to generate the connection verification support information.

In addition, if many medical diagnostic imaging apparatuses and viewer apparatuses are connected to the inter-apparatus connection verification support system, the connection verification support information is accumulated in the web server apparatus. Thus, when a new viewer apparatus verifies connection with a medical diagnostic imaging apparatus, the viewer apparatus may reuse the connection verification support information having been used previously, if a certain condition is fulfilled such as one where both the medical diagnostic imaging apparatus and the viewer apparatus are of exactly the same types as those checked previously. In this case, the connection verification processing can be initiated immediately after only particular items are checked. Thus, the time and efforts required for the connection verification can be reduced more.

While certain embodiments have been described, these embodiments have been presented by way of example only, and are not intended to limit the scope of the inventions.

For example, the foregoing embodiments have been provided by taking a "viewer apparatus" as one example of the peripheral apparatus. However, as for examples of the "peripheral apparatus" other than the viewer apparatus, embodiments of the present invention can be also used to verify connection between a hospital information system (HIS) and a radiological information system (RIS) built in the same medical institution, or verify connection between an RIS and a server or printer connected to a communication network to which the RIS is connected.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An inter-apparatus connection verification support system comprising:
a medical diagnostic imaging apparatus configured to generate a medical image of a subject and to generate connection verification support information to be used by a connection-target apparatus to verify connection with the medical diagnostic imaging apparatus;
a peripheral apparatus expected to be connected with the medical diagnostic imaging apparatus via a communication network and configured to operate the medical image generated by the medical diagnostic imaging apparatus; and a web server apparatus configured to record the connection verification support information generated by the medical diagnostic imaging apparatus;
wherein the peripheral apparatus verifies connection with the medical diagnostic imaging apparatus by using the connection verification support information acquired from the web server apparatus;
wherein the medical diagnostic imaging apparatus includes processing circuitry configured to:
collect, as request item information, specification items matched with items requested by the peripheral apparatus from the specification information; and
identify measurement data in conformance to the request item information;
wherein the web server apparatus includes processing circuitry configured to:
receive request items and information on specifications of the medical diagnostic imaging apparatus; and
generate the connection verification support information to be used by the peripheral apparatus to verify the connection, on the basis of the specification information outputted from the medical diagnostic imaging apparatus and the request items outputted from the peripheral apparatus.

2. The inter-apparatus connection verification support system according to claim 1, wherein the peripheral apparatus is a viewer apparatus or a printer connected to the communication network, or a device included in any kind of management system built in a medical institution and connected to the communication network.

3. The inter-apparatus connection verification support system according to claim 2, wherein
the connection verification support information includes specification information of the medical diagnostic imaging apparatus and measurement data acquired in accordance with the specification information.

4. The inter-apparatus connection verification support system according to claim 1, wherein
the connection verification support information includes specification information of the medical diagnostic imaging apparatus and measurement data acquired in accordance with the specification information.

5. An inter-apparatus connection verification method comprising the steps of:
identifying a request items in a peripheral apparatus, which is configured to display a medical image generated by a medical diagnostic imaging apparatus, in verifying connection between the peripheral apparatus and the medical diagnostic imaging apparatus;
identifying, as request item information, a specification item matched with the request item from specification information of the medical diagnostic imaging apparatus, identifying measurement data in conformance to the request item information, and posting the request item information as connection verification support information on a web server apparatus;
causing the peripheral apparatus to acquire the connection verification support information posted on the web server apparatus and to perform matching of the connection verification support information with the request item; and
completing the verifying of the connection between the peripheral apparatus and the medical diagnostic imaging apparatus by completing the matching.

6. An inter-apparatus connection verification method comprising the steps of:
causing a peripheral apparatus, which is expected to be connected with a medical diagnostic imaging apparatus configured to generate a medical image, to identify a request item needed to verify connection with the medical diagnostic imaging apparatus, and send the request item to a web server apparatus;
causing the medical diagnostic imaging apparatus to acquire the request item from the web server apparatus and to identify measurement data in conformance to the request item;
identifying, as request item information, information matched with the request item from specification information of the medical diagnostic imaging apparatus, and posting the request item information as connection verification support information on the web server apparatus;
causing the peripheral apparatus to acquire the connection verification support information posted on the web server apparatus and to perform matching of the connection verification support information with the request item; and
completing the verifying of the connection between the peripheral apparatus and the medical diagnostic imaging apparatus by completing the matching.

* * * * *